(12) United States Patent
Vaughn et al.

(10) Patent No.: US 6,379,958 B1
(45) Date of Patent: Apr. 30, 2002

(54) SELECTED INSECT CELL LINE CLONES PROVIDING INCREASED YIELD OF BACULOVIRUSES AND GENE EXPRESSION PRODUCTS FROM RECOMBINANT BACULOVIRUSES

(75) Inventors: James L. Vaughn, Columbia; Kevin J. Hackett, Beltsville; Clay Deming, Fort Washington, all of MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/577,148

(22) Filed: May 24, 2000

(51) Int. Cl.$^7$ .................................................. C12N 5/06
(52) U.S. Cl. ...................................... 435/348; 435/948
(58) Field of Search ................................... 435/348, 948

(56) References Cited

U.S. PATENT DOCUMENTS 6,103,526 A * 8/2000 Smith et al. ................. 435/348

OTHER PUBLICATIONS

ATCC Catalogue. Cell Lines and Hybridomas. 8th edition. 1994. p. 166.*
Vaughn et al. In Vitro. 1977. vol. 13, No. 4, pp. 213–217.*
Smith et al. Proc. Natl. Acad. USA. Dec. 1985. vol. 82, pp. 8404–8408.*
Vaughn, J.L., et al., "In Vitro Production of Baculoviruses Selection of Cell Lines to Optimize Yields", *V11th International Colloquium on Invertebrate Pathology and Microbial Control Ivth International conference on Bacillus thuringiensis*, pp. 298–302, Sapporo, Aug. 23–28, 1998.

* cited by examiner

*Primary Examiner*—Sandra E. Saucier
*Assistant Examiner*—Vera Afremova
(74) *Attorney, Agent, or Firm*—M. Howard Silverstein; John D. Fado; Evelyn M. Rabin

(57) ABSTRACT

Three new insect cell lines have been established and characterized. The cloned cell lines are derived from IPLB-Sf-21AE and can grow in serum-free medium. When infected with baculovirus, the cell lines of the invention produce large quantities of baculovirus. Infection with recombinant baculovirus yields large quantities of expressed functional protein. In particular, cell lines deposited in ATCC as PTA-22O7, PTA-2206 and PTA-2205.

18 Claims, 1 Drawing Sheet

SELECTED INSECT CELL LINE CLONES PROVIDING INCREASED YIELD OF BACULOVIRUSES AND GENE EXPRESSION PRODUCTS FROM RECOMBINANT BACULOVIRUSES

BACKGROUND OF THE INVENTION

1. Field of the Invention

The present invention relates generally to cell lines which are generated from differentiated tissue of insects and which are susceptible to baculoviruses and may be used to replicate such viruses. The invention further relates to the use of such cell lines to replicate large numbers of baculoviruses and particularly, to replicate large numbers of genetically engineered baculoviruses, and to thus express large quantities of recombinant proteins. In addition, the invention relates to cell lines which tolerate the expression of a wide range of recombinant proteins including known toxins.

2. Description of the Relevant Art

Baculoviruses are considered a potentially important tool for managing insect pests and cell culture is a desired means of producing them. In nature, insects can become infected with baculovirus particles as a result of consuming food contaminated with baculovirus particles. These food-borne baculovirus particles are typically in the form of occlusion bodies (OB) which are composed of multiple viral particles embedded within a virus-encoded proteinaceous crystal. After ingestion, the protein crystal of the occlusion bodies dissolves, releasing individual virus particles which invade the epithelial cells that line the midgut. Viral replication takes place in the nuclei of the cells, and usually two forms of baculovirus, occluded and extracellular virus (ECV), are generated during replication. ECV is produced first and acquires an envelope as it buds out from the surface of the cell. The ECV can then infect other cells within the insect, including fat body cells, epidermal cells, and hemocytes. Following this initial stage of infection, virions are produced which are occluded in OB. OB formation continues until the cell ultimately dies or lyses. Some baculoviruses can infect virtually every tissue in the host insect so that at the end of the infection process, the entire insect is liquified, releasing extremely large numbers of OB which are then responsible for spreading the infection to other insects (1986. The Biology of Baculoviruses, Vol. I and II. Granados et al., Eds. CRC Press, Boca Raton, Fla.).

The first attempts to replicate baculoviruses in cell culture were in lines from the homologous insect species (Grace, T. D. C. 1967. In Vitro 3: 104–117; Goodwin et al. 1970. *J. Invertebr. Pathol.* 16: 284–288). However, Sohi et a. (1972. *J. Invertebr. Pathol.* 19: 51–61) and Granados et al. (1976. In: Invertebrate Tissue Culture, Applications in Medicine, Biology, and Agriculture, Kurstak et al., Eds. Academic Press, New York, N. Y., pages 379–389) soon demonstrated the replication of baculoviruses in cell lines from insect species other than the ones from which the viruses were isolated. Quiot (1976. *C. R. Acad. Sci. Ser. D*. 282: 465–467) reported a gypsy moth cell line that replicated an iridovirus and seven baculoviruses, but not the gypsy moth nuclear polyhedrosis virus (NPV). Goodwin et aL (1978. *In Vitro* 14: 485–494) reported that several cell lines developed from gypsy moth by very similar methods were quite different in their replication of baculoviruses. Some cell lines replicated the gypsy moth NPV; whereas, others did not replicate gypsy moth NPV but did replicate the *Autographa californica* nuclear polyhedrosis virus (AcNPV).

AcNPV, in particular, has a broad in vivo host range and will multiply in cell lines from a number of species of insects. Some of the cell lines in which AcNPV has been replicated are shown in Table 1. In addition to 11 genera and 12 species, the listed cell lines are from a number of different tissues such as blood cells and minced whole larvae. The relative merits of this large variety of cell diversity has not been adequately screened to categorize its potential for virus production or gene expression.

TABLE 1

Insect Cell Lines Susceptible to AcNPV

| Cell Line | Tissue of Origin | Species of Origin |
|---|---|---|
| IPLB-Ld-652Y | Pupal ovary | Lymantria dispar |
| IPLB-Sf-21 | Pupal ovary | Spodoptera frugiperda |
| BCIRL-Hz-AM3 | Pupal ovary | Helicoverpa zea |
| BCIRL-Hv-AM1 | Pupal ovary | Heliothis virescens |
| Tn-368 | Adult ovary | Trichoplusia ni |
| IZD-MB-0503 | Hemocytes | Mamestra brassicae |
| IPRI-Md-108 | Hemocytes | Malocosoma disstria |
| NIAS-MaBr-85 | Larval Fat Body | Mamestra brassicae |
| NIAS-LeSe-11 | Larval Fat Body | Leucania separata |
| IPLB-Tn-RR | Embryo | Trichoplusia ni |
| BTI-TN5B1-4 | Embryo | Trichoplusia ni |
| IPLB-LdEIt | Embryo | Lymantria dispar |
| UFL-Ag-286 | Embryo | Anticarsia gemmatalis |
| UCR-Se-1 | Neonate larvae | Spodoptera exigua |
| FPMI-Ms-5 | Neonate larvae | Manduca sexta |
| IPRI-Cf-1 | Neonate larvae | Choristoneura fumiferana |

The first comparison of AcNPV replication in cell lines from several species of insects was made by Lynn and Hink in 1980 (*J. Invertebr. Pathol.* 35: 234–240). Five cell lines known to be susceptible to AcNPV were evaluated using several parameters to measure performance. The cell line used in any in vitro system is an important element both in terms of the quality and the quantity of the final product. The selected cell line must be capable of growth in suspension in large volumes. The IZD-MB0503 line from *Mamestra brassicae* was the best of those tested based upon the yield of active polyhedra over several passages. However, cell lines from *Trichoplusia ni* Tn-368, produced polyhedra with specific activity closest to that of polyhedra produced in insect larvae. The line Sf-1254, from *Spodoptera frugiperda*, produced only about one-tenth the amount of ECV produced by most of the other cell lines. Thus, it would be difficult to use this line for production as either large volumes of culture supernatant would be required for seed virus or the virus would have to be concentrated.

The NPV of the gypsy moth is registered as a pesticide by EPA under the name GYPCHEK. Production of the virus for pest management is in insect larvae as the yields from cell lines developed by Goodwin (Goodwin et al. 1978, supra) have been too low and the process too costly. Therefore, cell lines for different gypsy moth tissues, embryonic and fat body, were developed by Lynn and screened for their production capabilities (Lynn et al. 1989. *Appl Environ. Microbiol.* 55: 1049–1051). A line from fat body, IPLB-LdFB, and one from embryos, IPLB-Elt, were compared with Goodwin's line from pupal ovary, IPLB-Ld-652Y. OBs produced in the three lines are shown in FIG. 1. Three strains of the virus were used in the studies. The LdFB cells produced the highest number of OBs regardless of the virus strain used, with the LdFB-Ab combination producing significantly more than any other combination. ECV was not produced in high titers in any cell-virus combination. $TCID_{50}s/ml$ ranged from $3.83 \times 10^3$ to $2.61 \times 10^5$ in IPLB-652Y depending on the virus strain used. These results were obtained in attached cultures and based upon them, the LdFB-Ab virus combination was considered the best for in vitro production. However, attempts to scale up suspension cultures of the LdFB cells have not been successful as the cells are very fragile, especially after infection. Yields in suspension culture were considerably less than in static culture. Volkman et al. (1984. *Appl. Environ. Microbiol.* 44:227–233) made a comparison similar to the Lynn studies using an immunoassay to detect infected cells. All of the cell lines tested responded linearly to virus dose; however, the dose range for Tn-368 cells, the most sensitive, was 4.5–5.5 $\log_{10}$ and the range for the least sensitive cells, from *L. dispar*, was 1.3–2.3 $\log_{10}$. Cell lines from *Bombyx mori* and *L. dispar* produced more than 99% single cell foci of infection. One possible interpretation of these results is that these cell lines do not produce much ECV, making them less suitable for production.

In the most extensive screening of variation in virus susceptibility, Miltenburger et al. (1984.*Z. Naturforsch* 39: 993–1002) challenged over 80 primary cultures derived from *Cydia pomonella*, apple codling moth, with *Choristoneura murinana* NPV and *C. pomonella* granulosis virus (GV). The primary cultures were obtained from embryonic tissues or tissues from fourth or fifth instar larvae. Several methods were employed for subculturing the cells to obtain a variety of cell populations in the new cultures. The majority of cultures supported some level of NPV replication, but only nine were judged to be very good. Of these nine, four were unstable, showing significant decline in the number of polyhedra produced within five passages. Seven supported at least minimal GV replication, but only two produced capsules as revealed by electron microscopy. One supported better than minimal, but not exceptional, GV replication.

In comparison with the AcNPV, the *Helicoverpa zea* NPV is host specific, infecting only *H. zea* and closely related species. McIntosh and colleagues (Lenz et al. 1991. *J. Invertebr. Pathol.* 57: 227–233) compared virus production in two uncloned lines and in cloned lines obtained from the parent lines. There was no difference in the amount of ECV produced in the two uncloned lines and only about a two-fold difference in the OB produced. However, cloned cell lines were obtained that produced 5 times more polyhedra per ml of culture than the parent line. The number of polyhedra per infected cell was not significantly different, thus the increase in yield/ml apparently was achieved by eliminating non-producing cells. The amount of ECV expressed as plaque forming units/ml was not increased in the cloned cells. Overall in this study the yield of OBs from the best cloned cell line was about 85-fold better than from the poorest producing cell line.

In addition to needing cell lines capable of producing high yields of insect viruses for use in pest control research, baculoviruses are also used to produce large amounts of recombinant, foreign proteins of medical, pharmaceutical, and veterinary importance in various insect cell lines. "Recombinant, foreign proteins" refer to peptides or proteins, unrelated to, or, other than, the proteins of the wild-type baculovirus and to peptides or proteins which are not intrinsically found in the wild-type baculovirus in either the position or copy number provided in the genetically engineered baculovirus. The desired product is an expressed protein that is produced in large amounts and that is as similar to the natural protein as possible, including necessary post-translation processing and modification. Growing cells in suspension in large volumes and in medium free of fetal bovine serum (FBS) is preferred in order to facilitate downstream recovery and purification of expressed protein and to reduce costs (Vaughn, J. 1999. In: Encyclopedia of Bioprocess Technology: Fermentation, Biocatalysis, and Bioseparation, Flickinger et al., Eds. John Wiley & Sons, Inc., NY, pages 1444–1457).

Differences in yields of expressed gene products from engineered baculoviruses among cell lines have been reported. Hink et al. (1991. *BiotechnoL Prog.* 7: 9–14) compared the expression of three recombinant proteins in twenty-three different cell lines. For each protein, the yield varied among the cell lines and no one cell line produced the highest yields for all three proteins. However, the IZD-MB0503 would be a good compromise for producing all three proteins in a single line. A clone from this line that grew well in suspension was selected and cultured in a ten liter fermentor.

Two of the same lines, IPLB-Hv-T1 and IPLB-LdElta, also were tested by Betenbaugh et aL. (1991. *Biotechnol. Prog.* 7: 462–467) for their ability to produce the recombinant protein β-galactosidase and a porcine rotaviral protein, VP4.In this study, the yields of β-galactosidase from both cell lines exceeded that of Sf-9 in activity/ml culture. However, in terms of activity/mg of protein produced, only the yield from LdElta exceeded that of Sf-9. Yields from Sf-9 cells obtained in this study were lower than those reported by Hink et al. (supra), possibly due to differences in culture conditions. Total production of VP4 in LdElta cells was almost double that of Sf-9 cells. More of the VP4 was released from the SF-9 cells than from the LdElta cells; 95% and 88%, respectively. Both cell lines grew in suspension culture, but the LdElta cells tended to aggregate, which could present a problem in larger vessels.

Recently, a clone of an embryonic cell line T. ni developed by Granados and co-workers (Granados et al. 1994. *J. Invertebr. Pathol.* 64: 260–266) has been shown to produce high yields of wild type virus and several recombinant proteins. In the first 3–6 virus passages, polyhedra production was greater than 500 polyhedralcell with specific activity equal to that of polyhedra produced in larvae. As with other cell lines, both the number of polyhedra and the specific activity declined after the $6^{th}$ virus passage, with production stabilizing at about 100 polyhedra per cell after the $19^{th}$ passage. The cloned line, BTI-TN-5B1–4, "high five", originally developed as a substrate dependent line, has been adapted to grow in suspension.

Insect cell lines are used as a culture system for the production of diagnostics and vaccines used in human and veterinary medicine. Hundreds of recombinant proteins have been expressed in insect cells and they are immunogenically, antigenically, and functionally similar to the native proteins. Among the post-translational processing steps that have been shown to occur in insect cells are fatty acid acylation, phosphorylation, and-glycosylation (Luckow, V. A. 1995. In: Baculoviruses Expression Systems and Biopesticides, Shuler et al., Eds. Wiley-Liss, New York, N.Y. , pages 51–90). The full nature of the glycosylation of proteins in insect cells is unclear. Most of the proteins recovered from insect cell cultures migrated faster on SDS-PAGE gels than the native protein, indicating a lower molecular weight because of incomplete post-translational modification. N-glycosylation has been described in many baculovirus-cell systems. In question is the ability of insect cells to produce proteins with complex oligosaccharides containing sialic acid residues. The absence of these residues can alter the biological activity of the protein. Davis and Wood (1995. *In Vitro Cell. & Develop. Biol.* 31: 659–663) examined the glycosylation of the human placental secreted alkaline phosphatase in insects and in the insect cell lines Sf-21, TN-368, and BTI-Tn-5B1–4. In the insect larvae, the protein contained complex oligosaccharide having sialic acid, but, that produced in the cell lines had only simple-type glycans. Davidson and Casttellino (1991. *Biochemistry* 30: 6689–6696) reported that in the human plasminogen produced in the cell line IZD-MB0503, *M. brassicae*, 63% of the oligosaccharides were of the complex type. These findings indicate that if the recombinant protein requires the complex oligosaccharide, additional cell lines should be tested. Other post-translational modifications may also require choosing a cell line other than one of those commonly used.

Thus, insect cell lines can be an economical means for obtaining high yields of bacculovirus and large quantities of recombinant proteins. Unlike many mammalian cells used for this purpose, they grow readily in suspension, and do not require a special atmosphere. Therefore, they can be grown in large stirred tanks with minimal specialized equipment. They infect only arthropods and therefore pose no risk to mammals. Yields of protein from baculovirus expression vectors in insect cell cultures are 20–250 times higher than those from mammalian cells. There are a number of protein-free media available from commercial supplies and the yields of foreign gene products from cells grown in these media generally have been comparable to yields in FBS-supplemented media. The baculovirus-insect cell system has been used with over five hundred genes; ninety-five percent of the expressed proteins have been biologically active (Vaughn, J., supra). However, although many cell lines have been described in the art, the need exists for new cell lines as a means for producing high yields of virus and for expressing and obtaining large quantities of a wide range of functional proteins.

Accordingly, the present invention provides cell lines which can be used to generate large quantities of genetically engineered baculovirus and large quantities of functional expressed protein.

SUMMARY OF THE INVENTION

We have now discovered novel cell lines which are useful for the production of large quantities of viral agents (viruses, viral particles, and/or occlusion bodies) or mixtures thereof in vitro.

In accordance with this discovery, it is an object of the invention to provide novel cell lines and a method of using them to produce high yields of viral agents, particularly baculoviruses. The viral agents may be employed as biological control agents.

It is also an object of the invention to provide cell lines which are effective for the production of functional expressed protein.

It is a further object of the invention to provide a method of using the cell lines for the production of genetically engineered baculovirus which express foreign proteins of medical, pharmaceutical, and veterinary importance.

Another object of the invention is to provide cell lines which are tolerant of a wide range of recombinant products.

Other objects and advantages of this invention will become readily apparent from the ensuing description.

DETAILED DESCRIPTION OF THE INVENTION

Figure 1:
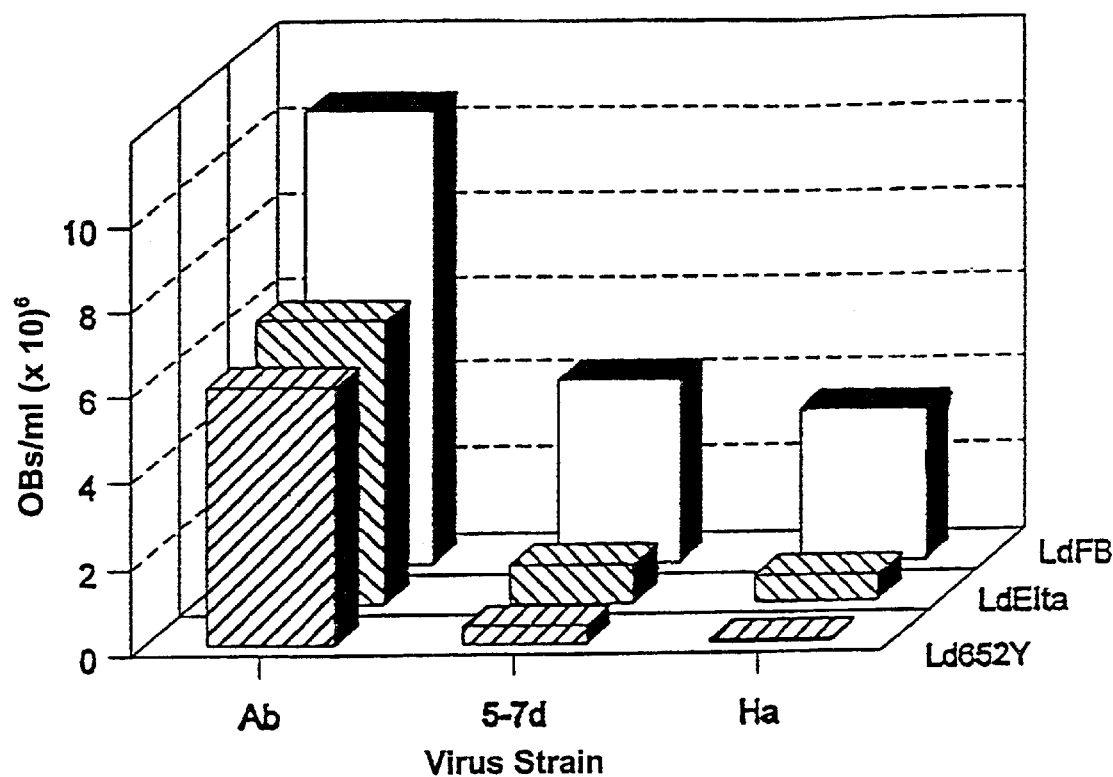
FIG. 1 compares the number of OBs produced in three different gypsy moth cell lines after infection with three different viruses. The cell lines compared are: IPLB-LdFB, derived from gypsy moth fat body; IPLB-Elt, from embryos, and IPLB-Ld-652Y, from pupal ovary. The cell lines were infected with three different strains of gypsy moth NPV: Ab, 5–7d, and Ha. Cells were distributed at $7.4 \times 10^4$ cells/well and inoculated at a multiplicity of 1 $TCID_{50}$/cell. The number of OBs were measured by suspending the cells in sterile distilled water, adding sodium dodecyl sulfate to a final concentration of 1% and allowing the OBs to settle overnight. The number of OBs in a random area of each dish was counted with an inverted phase-contrast microscope on day 7. Results are presented as the number of OBs $\times 10^6$ per ml.

This invention provides cloned cell lines which are susceptible to baculovirus replication and which yield large quantities of wild-type and genetically engineered baculovirus. In particular, the invention provides cell lines which can be used to obtain high yields of expressed recombinant proteins. Because the cell lines support post-translational modifications required for optimal function, the expressed proteins obtained from these cell lines are functional and have a high specific activity. Particularly provided are cell lines which have the capability of expressing a wide range of recombinant functional proteins.

Clones derived from single cells were obtained from the insect cell line, IPLB-Sf-21-AE, originating from *Spodoptera fugiperda*. The clones were obtained by picking isolated colonies from agarose plates according to the method of McIntosh et al. (1974. *In Vitro* 10: 1–5). Isolation was repeated three times for each clone.

Production of the viruses and baculoviruses in the cell lines is accomplished using cell culture techniques well known in the art. The cloned cell lines are provided in a culture medium in vitro, inoculated with virus or baculovirus, and incubated a sufficient time and under conditions effective to allow production of viral agents. Following incubation, the viral agents so produced are collected or harvested and recovered by techniques conventional in the art. The culture conditions including cell density, multiplicity of infection, time, temperature, media, etc. are not critical and may be readily determined by the practitioner skilled in the art. The term "viral agent" is defined herein to include viruses, viral particles, and occlusion bodies, or the nucleic acid therefrom as well as mixtures thereof, e.g.,. viruses and occlusion bodies. Without being limited thereto, the cell lines may be used to produce the virus and OB of baculoviruses, particularly natural or recombinant AcNPV. However, it is understood that other viruses or baculoviruses may be produced.

The clones were screened for their ability to replicate the natural AcNPV and two recombinant viruses, AcAalt and AcJHE (provided by Dr. Bruce Hammock, University of California-Davis). As discussed above, baculovirus replication results in the production of two forms of the virus. The most obvious is the incorporation within the infected cell of infectious virus particles into a protein crystal called an occlusion body (OB). The other form is the release of individual virus particles, extracellular virus (ECV), from the infected cell into the surrounding fluids, insect blood, or cell culture medium. The two forms of the virus are measured in different ways because of the way they infect the insect. From sixteen cell clones screened, three, Cl 3, Cl 5 and Cl 9, were found to produce more viral OB than either the parent line 21-AE or the commercially available cloned cell line Sf-9, derived from parent line 21-AE. When infected with the recombinant virus AcJHE, these clones produced more OB than either 21-AE or Sf-9.

In an alternative embodiment, the cell lines of the invention may be inoculated with genetically engineered baculoviruses to express foreign proteins or polypeptides of medical, pharmaceutical, or veterinary importance. The cell lines of the invention produces substantially high yields of baculoviruses. Heterologous nucleotide sequences encoding a peptide or protein may be inserted into the baculovirus DNA, such as operably coupled to or under the control of the polyhedrin promoter, so that the foreign peptide or protein is expressed upon culture of the cell line infected with the recombinant virus. A variety of techniques have been described for the preparation of recombinant baculovirus expression vectors (See Vaughn, J. 1999, supra; Frieson et al. 1986. In: The Molecular Biology of Baculoviruses, Doerfler et al., Eds. Springer-Verlag, Berlin, pages 31–49; Kool et aL 1993. *Arch. Virol.* 130: 1–16). Following inoculation of the cell line with the recombinant baculovirus and incubation for a sufficient time to allow expression, the foreign protein of interest may be subsequently recovered from the culture using conventional techniques.

Recombinant product was measured in these clones and expression of the JHE gene in these clones, estimated by a calorimetric method, was found to be superior to that observed in 21-AE or in the Sf-9 clone. The clones grew well in suspension culture either on commercial serum-free or low-cost medium being developed at the Insect Biocontrol Laboratory. Therefore, based on their ability to replicate both wild-type and recombinant AcNPV and expressed product from the genetically engineered viruses, clones Cl 3, Cl 5, and Cl 9 are excellent candidates to be used for the production of gene products for human and veterinary medicine or for the production of insect viruses for pest management.

The cell lines were deposited with the American Type Culture Collection (ATCC), 10801 University Blvd., Manassas, Va. 20110–2209 on Jul. 7, 2000, under accession numbers PTA-2207 (Cl3), PTA-2206 (Cl5), and PTA-2205 (Cl9).

The subject cell lines have been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject cell line deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the cell line. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

In a preferred embodiment, the present invention encompasses any cell lines that correspond in characteristics to the cell lines, IBL-SF-21AE-Cl3, IBL-SF-21AE-Cl5, and IBL-SF-21AE-Cl9, deposited as PTA-2207, PTA-2206, and PTA-2205, respectively.

These three novel cloned cell lines described herein display characteristics that make them valuable for research purposes and for commercial applications. The cell lines may be used for replicating baculoviruses, which may be used as insecticides, and for the production of recombinant proteins, including vaccines, antibodies, antitoxins, pharmaceuticals, and the like.

EXAMPLES

The following examples serve as further description of the invention and methods for practicing the invention. They are not intended as being limiting, rather as providing guidelines on how the invention may be practiced.

Example 1

Cell Culture and Cell Cloning Methods

These novel cloned cell lines are grown in suspension by methods known to those of skill in the art; the method given here is for illustration. The cultures are grown in 250 ml disposable Erlenmyer flasks. The insect cell culture medium used is IPL-41 (GIBCO-BRL Life Technologies, Inc., Gaithersburg, MD 20884) supplemented with 10% FBS (Hybri-Max or 10% serum replacement, Cat.# CPSR-3, from Sigma Chemical Co.,St. Louis, MO; Vaughn et al. 1989. *In Vitro Cell. Dev. Biol.* 25: 143–145). The cells are protected from shear forces by the addition of 1 gm of Pluronic F-68 (GASF Corp., Parsippany, N. J.) per liter of medium. A culture is initiated by seeding 100 ml of medium with $0.3 \times 10^6$ cells/ml and incubating at 28 °C. on an orbital shaker operated at 140 rpm. The cell growth was determined by removing three 0.5 ml samples daily and counting the cells with the aid of a microscope. Cell viability was determined by trypan blue exclusion.

The insect cell line IPLB-Sf-21AE was cloned by mixing diluted cell suspensions with a semisolid growth medium containing agarose at a final concentration of 0.5%. This cell suspension was dispensed into 60 mm culture dishes over a base layer of growth medium containing 2% agarose. When the cell layer was partially solidified, the dishes were sealed with tape and incubated in air at 28 °C. until small visible colonies appeared. Well isolated colonies were removed with a stenile Pasteur pipet and the cells suspended in liquid growth medium. The process was repeated twice more.

Following the third plating, the selected clones were expanded in growth medium and samples were stored in liquid nitrogen. Growth results for two clones, Cl 3 and Cl 9, when grown in IPL-41 medium supplemented with 10% FBS or in HYQ SFX serum-free medium are shown in Table 2.

TABLE 2

Growth of Clones Cl 3 and Cl 9

| Clone | Medium | Inoculum ($\times 10^6$) | Days in Culture | Final Cell Density ($\times 10^6$) |
|---|---|---|---|---|
| Cl 3 | IPL-41 + 10% FBS | 0.3 | 7 | 6.79 |
| Cl 9 | IPL-41 + 10% FBS | 0.3 | 10 | 7.90 |

TABLE 2-continued

Growth of Clones Cl 3 and Cl 9

| Clone | Medium | Inoculum (× 10⁶) | Days in Culture | Final Cell Density (× 10⁶) |
|---|---|---|---|---|
| Cl 3 | HYQ SFX serum-free | 0.3 | 7 | 2.17 |
| Cl 9 | HYQ SFX serum-free | 0.3 | 7 | 2.19 |

Example 2

Production of AcNPV Baculovirus; Determination of ECV

The amount of extracellular virus (ECV) produced by the individual cell clones was determined by an end point dilution method described by Lynn (Lynn, D. E. 1992. *Biotechniques* 13: 282–285). The titration was carried out in 96 well cell culture plates. Each of 84 wells was seeded with approximately 2000 cells suspended in fresh culture medium. Ten fold virus dilutions were prepared in the remaining row using an EDP electronic pipet (Rainin). A single row of 12 wells was inoculated with 10 μl of a particular virus dilution, resulting in six rows representing each of the six virus concentrations being tested. One row was not inoculated and served as the control. The plates were closed and sealed with tape and incubated at 27° C. for 4 days. The plates were then examined with a low power inverted phase microscope and the presence of OBs determined. The plates were reexamined at 1–3 day intervals until 10 days post infection. The estimated ECV produced was expressed as the number of viral units causing 50% infection produced per ml culture ($TCID_{50}$) and was calculated with a BASIC computer program with Karbers method for calculating 50% endpoints.

The extracellular wild type and recombinant virus produced in Clone 3, expressed as the $TCID_{50}$, is shown below in Table 3.

TABLE 3

ECV Produced in Clone 3

| VIRUS | $TCID_{50}$ |
|---|---|
| AcNPV-WT | $3.16 \times 10^7$/ml |
| AcNPV-JHE | $1.21 \times 10^7$/ml |
| AcNPV-AaIT | $3.83 \times 10^5$/ml |

Example 3

Occlusion Bodies Assay

The susceptibility of clones Cl 3, Cl 5, and Cl 9, to viral infection while in serum-free medium was also measured by an occlusion body assay. The cloned cell lines were seeded into 6 well culture dishes at a density resulting in 70–80% confluency for each clone and inoculated with virus at an MOI of 0.1 and 1.0 $TCID_{50}$. Seven days after infection, the culture medium was removed without disturbing the cells and stored frozen until it could be assayed for ECV. The infected cells were suspended in distilled water in order to lyse the cells and release the OBs. The suspended cells were mixed thoroughly and allowed to settle in the culture plate on a vibration free surface. The OB in randomly selected areas of the culture plate were counted with the aid of a low power microscope containing a calibrated ocular grid. The numbers of OB counted were converted to numbers of OB per ml culture based upon the ratio of number of OB in the area counted vs. total area of the culture dish and the volume of the culture.

Results of the screening of some clones are shown in Table 4. Growth of wild type virus (AcNPV-WT) and the recombinant viruses AcNPV-JHE and AcNPV-AaIT which produce recombinant juvenile hormone esterase and recombinant scorpion toxin, respectively, was determined by OB measurements. Wild type virus grew in Cl 3, Cl 5, and Cl 9 as well as or better than the cloned cell line Sf9, which is sold commercially and widely used in the art. Growth of the recombinant virus AcNPV-JHE was better in Cl 3, Cl 5, and Cl 9 than in Sf9. AcNPV-AaIT grew best in Cl 3.

TABLE 4

Occlusion Bodies* Produced in Selected Clones of the Cell Line Sf-21AE

| | CELL LINE | | | | |
|---|---|---|---|---|---|
| VIRUS | Sf-21AE | Sf-9 | Clone 3 | Clone 5 | Clone 9 |
| AcNPV-WT | 7.76 | 12.20 | 12.10 | 11.10 | 13.40 |
| AcNPV-JHE | 0.98 | 1.85 | 4.80 | 3.35 | 3.73 |
| AcNPV-AaIT | 2.12 | 2.04 | 9.96 | 3.59 | 4.49 |

*OB × 10⁶ per ml

Example 4

Production of Juvenile Hormone Esterase

The amount of juvenile hormone esterase (JHE) produced by genetically engineered AcNPV virus (AcNPV-JHE) in Sf-21AE cell culture was determined using a colorimetric method (Huang et aL 1993. *Pharmaceutic. Res.* 10(5): 639–647; McCutchen et al. 1995. *Molec. Biol.* 25(1): 119–126). The method exploits the ability of the esterase to cleave a surrogate juvenile hormone (1-heptylthioacetothioate). In the surrogate, a thiol ester moiety was substituted for the ester moiety of juvenile hormone (JH), and the 2,3-olefin of JH was replaced with thioether. Nucleophilic attack by JHE at the carbonyl functional group of the surrogate releases methanethiol which cleaves the disulfide bond of Elman's Reagent [5,5'-dithio-bis(2-nitrobenzoic acid)], resulting in a chromophore that can be detected at 405 nm. A spectral plate reader was used to detect the chromophore. The hydrolysis reaction was carried out at 23° C. and measured in a continuous assay using a 96-well microtiter plate (Dynatech Laboratories, Virginia, VA) with a microtiter plate reader (Dynex MRX, Chantilly, Va.). AcNPV-JHE virus, standard JHE, and surrogate juvenile hormone reagent were obtained courtesy of Dr. Bruce Hammock, University of California-Davis.

JHE production in the parent cell line, Sf-21AE, was compared with JHE production in clones Cl 3 and Cl 9, and Sf-9, a commercially available cell line. Using direct ratios of $V_{max}$ O.D. levels for comparison, there was 1.2- to 1.7-fold higher production of JHE by Cl 3, 1.2- to 1.6-fold higher production by Cl 9, and 0.8- to 0.9-fold lower production by Sf-9 (Table 5).

TABLE 5

Comparative Production of JHE as Determined by $V_{max}$ O.D. Levels

| Cell Line | Experiment 1 | Experiment 2 |
|---|---|---|
| Cl 3 | .270 | .183 |
| Cl 9 | .257 | .243 |
| Sf-9 | .143 | .127 |
| Sf-21AE | .163 | .150 |

It is understood that the foregoing detailed description is given merely by way of illustration and that modifications and variations may be made therein without departing from the spirit and scope of the invention.

We claim:

1. An insect cell line with all of the identifying characteristics of the cell line designated IBL-Sf-21AE-Cl 3, deposited under the ATCC accession number PTA-2207.

2. An insect cell line with all of the identifying characteristics of the cell line designated IBL-Sf-21AE-Cl 3, deposited under the ATCC accession number PTA-2207, and having all or any or at least one of the following characteristics:
   a. supports production of viral agents of baculoviruses, comprising viruses, viral particles, occlusion bodies, and mixtures thereof;
   b. supports expression of recombinant foreign protein after infection by a recombinant baculovirus;
   c. grows in suspension or shaker flask cell culture;
   d. grows in serum-free medium; and
   e. grows in said serum-free medium and retains the ability to support replication of baculovirus.

3. The insect cell line of claim 2 wherein at least about $2.5 \times 10^6$ occlusion bodies are produced per ml of medium after infection by the recombinant baculovirus.

4. The insect cell line of any one of claims 2–3 wherein the recombinant baculovirus is a recombinant AcNPV virus.

5. An insect cell line, wherein said insect cell line is a clone, derivative, mutant, or transfectant of the cell line IBL-Sf-21AE-Cl 3 (ATCC accession number PTA-2207), wherein the cells of said cell line, when cultured, grow continuously and retain the identifying characteristics of the insect cell line IBL-Sf-21AE-Cl 3 (PTA-2207) of claim 2.

6. An insect cell line designated IBL-Sf-21AE-Cl 3, deposited under the ATCC accession number PTA-2207.

7. An insect cell line with all of the identifying characteristics of the cell line designated IBL-Sf-21AE-Cl 5, deposited under the ATCC accession number PTA-2206.

8. An insect cell line with all of the identifying characteristics of the cell line designated IBL-Sf-21AE-Cl 5, deposited under the ATCC accession number PTA-2206, and having all or any or at least one of the following characteristics:
   a. supports production of viral agents of baculoviruses, comprising viruses, viral particles, occlusion bodies, and mixtures thereof;
   b. supports expression of recombinant foreign protein after infection by a recombinant baculovirus;
   c. grows in suspension or shaker flask cell culture;
   d. grows in serum-free medium; and
   e. grows in said serum-free medium and retains the ability to support replication of baculovirus.

9. The insect cell line of claim 8 wherein at least about $2.5 \times 10^6$ occlusion bodies are produced per ml of medium after infection by the recombinant baculovirus.

10. The insect cell line of any one of claims 8–9 wherein the recombinant baculovirus is a recombinant AcNPV virus.

11. An insect cell line, wherein said insect cell line is a clone, derivative, mutant, or transfectant of the cell line IBL-Sf-21AE-Cl 5 (ATCC accession number PTA-2206), wherein the cells of said cell line, when cultured, grow continuously and retain the identifying characteristics of the insect cell line IBL-Sf-21AE-Cl 5 (PTA-2206) of claim 8.

12. An insect cell line designated IBL-Sf-21AE-Cl 5, deposited under the ATCC accession number PTA-2206.

13. An insect cell line with all of the identifying characteristics of the cell line designated IBL-Sf-21AE-Cl 9, deposited under the ATCC accession number PTA-2205.

14. An insect cell line with all of the identifying characteristics of the cell line designated IBL-Sf-21AE-Cl 9, deposited under the ATCC accession number PTA-2205, and having all or any or at least one of the following characteristics:
   a. supports production of viral agents of baculoviruses, comprising viruses, viral particles, occlusion bodies, and mixtures thereof;
   b. supports expression of recombinant foreign protein after infection by a recombinant baculovirus;
   c. grows in suspension or shaker flask cell culture;
   d. grows in serum-free medium; and
   e. grows in said serum-free medium and retains the ability to support replication of baculovirus.

15. The insect cell line of claim 14 wherein at least about $2.5 \times 10^6$ occlusion bodies are produced per ml of medium after infection by the recombinant baculovirus.

16. The insect cell line of any one of claims 14–15 wherein the recombinant baculovirus is a recombinant AcNPV virus.

17. An insect cell line, wherein said insect cell line is a clone, derivative, mutant, or transfectant of the cell line IBL-Sf-21AE-Cl 9 (ATCC accession number PTA-2205), wherein the cells of said cell line, when cultured, grow continuously and retain the identifying characteristics of the insect cell line IBL-Sf-21AE-Cl 9 (PTA-2205) of claim 14.

18. An insect cell line designated IBL-Sf-21AE-Cl 9, deposited under the ATCC accession number PTA-2205.

\* \* \* \* \*